(12) United States Patent
Limon

(10) Patent No.: US 8,002,817 B2
(45) Date of Patent: Aug. 23, 2011

(54) STENTS WITH HIGH RADIAL STRENGTH AND METHODS OF MANUFACTURING SAME

(75) Inventor: Timothy A. Limon, Cupertino, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 202 days.

(21) Appl. No.: 12/114,608

(22) Filed: May 2, 2008

(65) Prior Publication Data

US 2008/0275537 A1 Nov. 6, 2008

Related U.S. Application Data

(60) Provisional application No. 60/927,785, filed on May 4, 2007.

(51) Int. Cl.
*A61F 2/82* (2006.01)
(52) U.S. Cl. ...................... 623/1.15; 623/1.16
(58) Field of Classification Search .............. 623/1.11, 623/1.15, 1.16
See application file for complete search history.

(56) References Cited

U.S. PATENT DOCUMENTS

| | | | |
|---|---|---|---|
| 6,206,911 B1 * | 3/2001 | Milo | 623/1.15 |
| 6,312,459 B1 * | 11/2001 | Huang et al. | 623/1.15 |
| 2003/0023301 A1 * | 1/2003 | Cox et al. | 623/1.15 |
| 2006/0020330 A1 | 1/2006 | Huang et al. | |
| 2006/0076708 A1 | 4/2006 | Huang et al. | |
| 2006/0265050 A1 | 11/2006 | Morris et al. | |
| 2007/0293938 A1 | 12/2007 | Gale et al. | |

FOREIGN PATENT DOCUMENTS

| | | |
|---|---|---|
| EP | 1 859 823 | 11/2007 |
| WO | WO 2007/021706 | 2/2007 |
| WO | WO 2007/142750 | 12/2007 |
| WO | WO 2007/146354 | 12/2007 |
| WO | WO 2007/149457 | 12/2007 |

OTHER PUBLICATIONS

International Search Report for PCT/US2008/062607, mailed Aug. 5, 2008, 6 pgs.

* cited by examiner

*Primary Examiner* — Thomas J Sweet
*Assistant Examiner* — Seema Swaminathan
(74) *Attorney, Agent, or Firm* — Squire, Sanders & Dempsey (US) LLP

(57) ABSTRACT

Polymeric stents having fracture toughness and resistance to recoil after deployment are disclosed along with methods of manufacturing such stents. Improvements to mechanical characteristics and other improvements may be achieved by having polymer chains within individual stent struts oriented in a direction that is closer to or in line with the axis of the individual stent struts. The desired orientation of polymer molecules may be achieved by one or any combination of extruding polymers into hollow tubes to induce axially oriented polymer chains, applying a tensile load to polymer tubes to induce axially oriented polymer chains, and radially expanding polymer tubes to induce circumferentially oriented polymer chains. Stent patterns include struts defining diamond shaped cells and/or W-shaped cells.

14 Claims, 7 Drawing Sheets

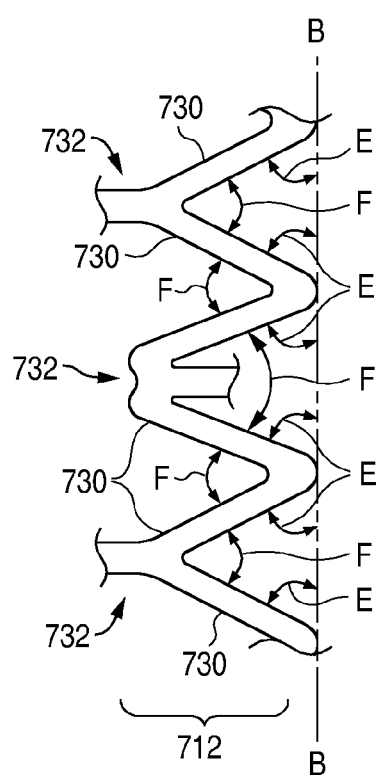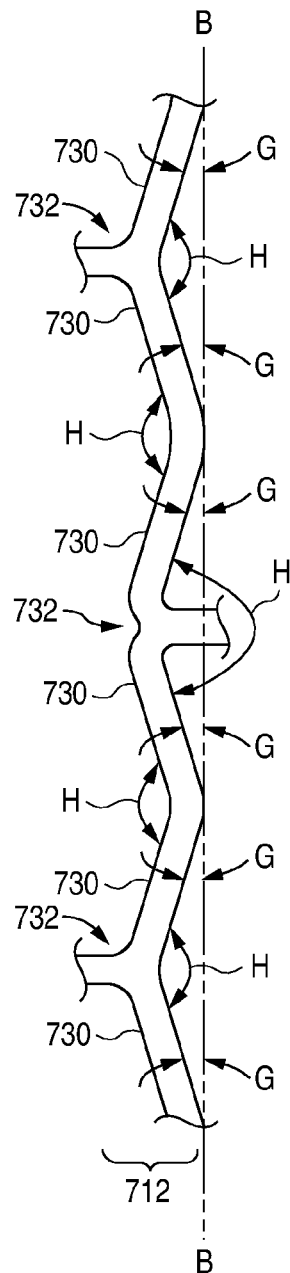
FIG. 7  FIG. 8

US 8,002,817 B2

STENTS WITH HIGH RADIAL STRENGTH AND METHODS OF MANUFACTURING SAME

This application claims the benefit of prior U.S. Provisional Application No. 60/927,785, filed May 4, 2007, the entire contents of which is incorporated by reference.

BACKGROUND OF THE INVENTION

1. Field of the Invention

This invention relates to expandable endoprostheses, and more particularly to polymeric stents and methods of manufacturing polymeric stents.

2. Description of the State of the Art

An "endoprosthesis" corresponds to an artificial device that is placed inside the body, more particularly, within an anatomical lumen. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil.

In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

However, there are potential shortcomings in the use of polymers as a material for implantable medical devices, such as stents. There is a need for a manufacturing process for a stent that addresses such shortcomings so that a polymeric stent can meet the clinical and mechanical requirements of a stent.

SUMMARY OF THE INVENTION

Briefly and in general terms, the present invention is directed to an endoprosthesis and a method of making an endoprosthesis. In aspects of the present invention, the method comprises radially deforming a polymer tube to increase radial strength of the polymer tube. The method further comprises forming linear ring struts and curved hinge elements from the deformed polymer tube, the ring struts connected to each other by the hinge elements, the ring struts and the hinge elements defining a plurality of rings, the hinge elements adapted to allow the rings to move from a non-deformed configuration to a deformed configuration. When the rings are in the non-deformed configuration, the ring struts are oriented relative to each other at an interior angle greater than 100 degrees.

In further aspects of the present invention, the interior angle is between about 124 degrees and about 130 degrees. In other aspects, an outer diameter of the polymer tube after the radial deformation is greater than or equivalent to about five times an inner diameter of the polymer tube prior to the radial deformation. In yet other aspects, an outer diameter of the polymer tube after the radial deformation is greater than or equivalent to about six times an inner diameter of the polymer tube prior to the radial deformation.

In detailed aspects of the present invention, when the rings are in the non-deformed configuration, each ring strut is oriented at a non-zero angle less than about 40 degrees relative to the direction in which the polymer tube was radially deformed. In other detailed aspects, each ring has a center point, at least two of the center points defines a central axis, and the method further comprises forming link struts that connect the rings together, the link struts oriented parallel or substantially parallel to the central axis, wherein the ring struts, hinge elements, and link struts define a plurality of W-shaped closed cells, each W-shaped cell touching six other W-shaped cells, each W-shaped cell having a perimeter that includes eight of the ring struts, two of the link struts, and ten of the hinge elements.

The endoprosthesis, in aspects of the present invention, comprises linear ring struts and curved hinge elements, the ring struts connected to each other by the hinge elements, the ring struts and the hinge elements defining a plurality of rings, the hinge elements adapted to allow the rings to move from a non-deformed configuration to a deformed configuration. When the rings are in the non-deformed configuration, the ring struts are oriented relative to each other at an interior angle greater than 100 degrees.

In other aspects of the present invention, the method of making an endoprosthesis comprises radially expanding a polymer tube so that an outer diameter of the polymer tube after expansion is greater than about four times an inner diameter of the polymer tube prior to expansion. The method also comprises forming ring struts and link struts from the radially expanded polymer tube, the ring struts defining a plurality of rings capable of moving from a non-deformed configuration to a deformed configuration, each ring having a center point, at least two of the center points defining a central axis, the link struts oriented parallel or substantially parallel to the central axis and connecting the rings together, the link struts and the ring struts defining W-shaped closed cells, each W-shaped cell abutting six other W-shaped cells. When the rings are in the non-deformed configuration, the ring struts are oriented relative to each other at an interior angle greater than 100 degrees.

The endoprosthesis, in aspects of the present invention, comprises ring struts and link struts formed from a radially expanded polymer tube having an outer diameter after expansion that is greater than about four times the inner diameter of the polymer tube prior to expansion, the ring struts defining a plurality of rings capable of moving from a non-deformed configuration to a deformed configuration, each ring having a center point, at least two of the center points defining a central axis, the link struts oriented parallel or substantially parallel to the central axis and connecting the rings together, the link struts and the ring struts defining W-shaped closed cells, each W-shaped cell abutting six other W-shaped cells. When the rings are in the non-deformed configuration, the ring struts are oriented relative to each other at an interior angle greater than 100 degrees.

In further aspects of the present invention, the interior angle is between about 124 degrees and about 130 degrees. In other aspects, the outer diameter of the polymer tube after expansion is greater than or equivalent to about six times the inner diameter of the polymer tube prior to expansion. In detailed aspects, when the rings are in the non-deformed configuration, each ring strut is oriented at angle between about 25 degrees and about 28 degrees relative to a plane perpendicular to the central axis. In other detailed aspects, the link struts and the ring struts are equivalent or substantially equivalent in length. In further detailed aspects, the ring struts on each ring define a series of crests and troughs that alternate with each other, each crest on each ring connected by one of the link struts to another crest on another ring.

The features and advantages of the invention will be more readily understood from the following detailed description which should be read in conjunction with the accompanying drawings.

BRIEF DESCRIPTION OF THE DRAWINGS

FIG. 7 depicts a partial view of a ring from FIG. 4, showing the ring in a deformed configuration after being radially collapsed to a diameter less than the initial diameter.

FIG. 8 depicts a partial view of a ring from FIG. 4, showing the ring in another deformed configuration after manufacturing, the ring having been deployed at a diameter greater than the initial diameter.

DETAILED DESCRIPTION OF THE INVENTION

The various embodiments of the present invention relate to polymeric stents and methods of fabricating polymeric stents with favorable mechanical properties. The present invention can be applied to devices including, but is not limited to, self-expandable stents, balloon-expandable stents, stent-grafts, and grafts (e.g., aortic grafts).

Figure 1:
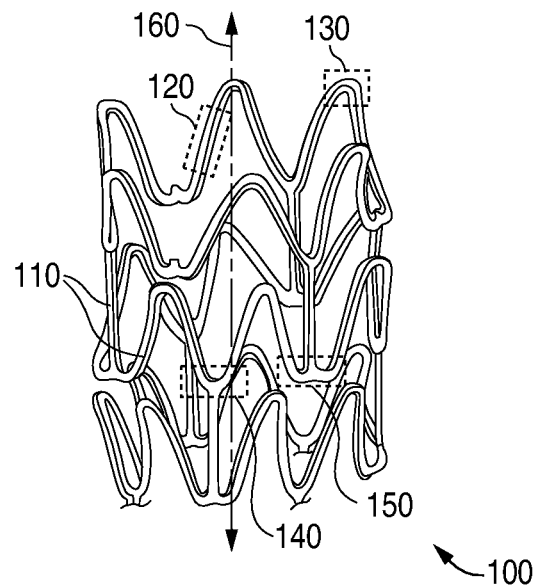
FIG. 1 depicts a stent.

FIG. 1 depicts a partial perspective view of an exemplary stent 100 that includes a pattern of a plurality of interconnecting structural elements or struts. Stent 100 has a cylindrical shape with an axis 160 and includes a pattern with a number of interconnecting structural elements or struts 110. Axis 160 extends through the center of the cylindrical shape. In general, a stent pattern is designed so that the stent can be radially compressed to allow for percutaneous delivery through an anatomical lumen, then deployed for implantation at the desired segment of the anatomical lumen. As used herein, deployment of the stent refers to radial expansion of the stent to implant the stent in the patient. The stresses involved during compression and deployment are generally distributed throughout various structural elements of the stent pattern.

The underlying structure or substrate of stent 100 is typically the primary source of the radial strength of the stent. The substrate can be completely or at least in part made from a biodegradable polymer or combination of biodegradable polymers, a biostable polymer or combination of biostable polymers, or a combination of biodegradable and biostable polymers. Additionally, a polymer-based coating applied over the substrate can include a biodegradable polymer or combination of biodegradable polymers, a biostable polymer or combination of biostable polymers, or a combination of biodegradable and biostable polymers.

Representative examples of polymers that may be used to fabricate or coat an implantable medical device of the present invention include, but are not limited to, poly(N-acetylglucosamine) (Chitin), Chitosan, poly(hydroxyvalerate), poly (lactide-co-glycolide), poly(hydroxybutyrate), poly(hydroxybutyrate-co-valerate), polyorthoester, polyanhydride, poly(glycolic acid), poly(glycolide), poly(L-lactic acid), poly (L-lactide), poly(D,L-lactic acid), poly(D,L-lactide), poly (caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating an implantable medical device include ethylene vinyl alcohol copolymer (commonly known by the generic name EVOH or by the trade name EVAL), poly(butyl methacrylate), poly (vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

Stent 100 may be fabricated from a polymeric tube or a polymeric sheet that has been rolled and bonded to form a tube. A stent pattern may be formed on the polymeric tube or sheet by laser cutting away portions of the tube or sheet, leaving only struts and other members that function as scaffolding to support the walls of an anatomical lumen. Representative examples of lasers that may be used include, but are not limited to, excimer, carbon dioxide, and YAG. In other embodiments, chemical etching may be used to form a pattern on a tube.

The pattern of stent 100 in FIG. 1 allows for radial expansion and compression and longitudinal flexure. The pattern includes struts that are straight or relatively straight, an example being a portion 120. In addition, patterns may include bending elements 130, 140, and 150. Bending elements bend inward when a stent is crimped to allow radial compression of the stent in preparation for delivery through an anatomical lumen. Bending elements also bend outward when a stent is deployed to allow for radial expansion of the stent within the anatomical lumen. After deployment, stent 100 is subjected to static and cyclic compressive loads from the vessel walls. Thus, bending elements may deform during use.

As indicated above, a stent has certain mechanical requirements. A stent must have sufficient radial strength to withstand structural loads, namely radial compressive forces, imposed on the stent as it supports the walls of a vessel or other anatomical lumen. In addition, the stent must possess sufficient flexibility to allow for crimping, deployment, and cyclic loading. Also, a sufficiently low profile, that includes diameter and size of struts, is important. As the profile of a stent decreases, the easier is its delivery, and the smaller the disruption of blood flow.

Polymers tend to have a number of shortcomings for use as substrate materials for stents. Compared to metals, the strength to weight ratio of polymers is smaller than that of metals. A polymeric stent with inadequate radial strength can result in mechanical failure or recoil inward after implantation into a vessel. To compensate for the relatively low modulus of polymers as compared to metals, a polymeric stent requires significantly thicker struts than a metallic stent, which can result in an undesirably large profile.

Another shortcoming of polymers is that many polymers, such as biodegradable polymers, tend to be brittle under physiological conditions or conditions within a human body. Specifically, some biodegradable polymers that have a glass transition temperature, Tg, above human body temperature of about 37° C. exhibit a brittle fracture mechanism in which there is little or no plastic deformation prior to failure. As a result, a stent fabricated from such polymers can have insufficient toughness for the range of use of a stent. In particular, it is important for a stent to be resistant to fracture throughout the range of use of a stent, i.e., crimping, delivery, deployment, and during a desired treatment period.

A potential problem with polymeric stents is mechanical creep deformation. Creep refers to the gradual deformation of a structure subjected to an applied load. It is believed that the delayed response of polymer chains to stress causes creep behavior in polymeric stents. Creep can cause a deployed stent to retract or recoil radially inward, reducing the effectiveness of a stent in maintaining desired vascular patency.

To address these and other problems, the mechanical properties of a polymer can be modified through various processing techniques, such as, by applying stress to a polymer. The application of stress can induce molecular orientation along the direction of stress which can modify mechanical properties along the direction of applied stress. For example, strength and modulus are some of the important properties that depend upon orientation of polymer chains in a polymer. Molecular orientation refers to the relative orientation of polymer chains along a longitudinal or covalent axis of the polymer chains.

A polymer may be completely amorphous, partially crystalline, or almost completely crystalline. A partially crystalline polymer includes crystalline regions separated by amorphous regions. The crystalline regions do not necessarily have the same or similar orientation of polymer chains. However, a high degree of orientation of crystallites may be induced by applying stress to a semi-crystalline polymer. The stress may also induce orientation in the amorphous regions. An oriented amorphous region also tends to have high strength and high modulus along an axis of alignment of polymer chains. Additionally, for some polymers under some conditions, induced alignment in an amorphous polymer may be accompanied by crystallization of the amorphous polymer into an ordered structure. This is known as stress induced crystallization.

As indicated above, due to the magnitude and directions of stresses imposed on a stent during use, it is important for the mechanical stability of the stent to have suitable mechanical properties, such as strength and modulus, in the axial and circumferential directions. Therefore, it can be advantageous to modify the mechanical properties of a polymeric tube or sheet substrate, to be used in the fabrication of a stent pattern, by induced orientation from applied stress in the axial direction, circumferential direction, or both. Since highly oriented regions in polymers tend to be associated with higher strength and modulus, it may be desirable to incorporate processes that induce alignment of polymer chains along one or more preferred axes or directions into fabrication of stents.

The degree of radial expansion, and thus induced circumferential orientation and radial strength, of a tube can be quantified by a radial expansion ratio:

$$RE = (\text{Outside Diameter of Expanded Tube}, OD_E) / (\text{Original Inside Diameter of Tube}, ID_O)$$

The RE ratio can also be expressed as a percent expansion:

$$\% RE = (RE - 1) \times 100\%$$

In some embodiments, a stent substrate in the form of a polymeric tube may be deformed by blow molding. In blow molding, the tube can be radially deformed or expanded by increasing a pressure in the tube by conveying a fluid into the tube. The fluid may be a gas, such as air, nitrogen, oxygen, or argon. The polymer tube may be deformed or extended axially by applying a tensile force by a tension source at one end while holding the other end stationary. Alternatively, a tensile force may be applied at both ends of the tube. The tube may be axially extended before, during, and/or after radial expansion.

In some embodiments, blow molding may include first positioning a tube in a tubular mold. The mold may act to control the degree of radial deformation of the tube by limiting the deformation of the outside diameter or surface of the tube to the inside diameter of the mold. The inside diameter of the mold may correspond to a diameter less than or equal to a desired diameter of the polymer tube. Alternatively, the fluid temperature and pressure may be used to control the degree of radial deformation by limiting deformation of the inside diameter of the tube as an alternative to or in combination with using the mold. The temperature of the tube can be heated to temperatures above the Tg of the polymer during deformation to facilitate deformation. The polymer tube may also be heated prior to, during, and subsequent to the deformation.

Properties of a polymer such as fracture toughness are affected by the overall degree of crystallinity and the number and size of crystal domains in a semi-crystalline polymer. It has been observed that fracture toughness is increased by having a large number of small crystal domains in a polymer surrounded by an amorphous domain. Such a crystal structure can also reduce or prevent creep.

Figure 2:
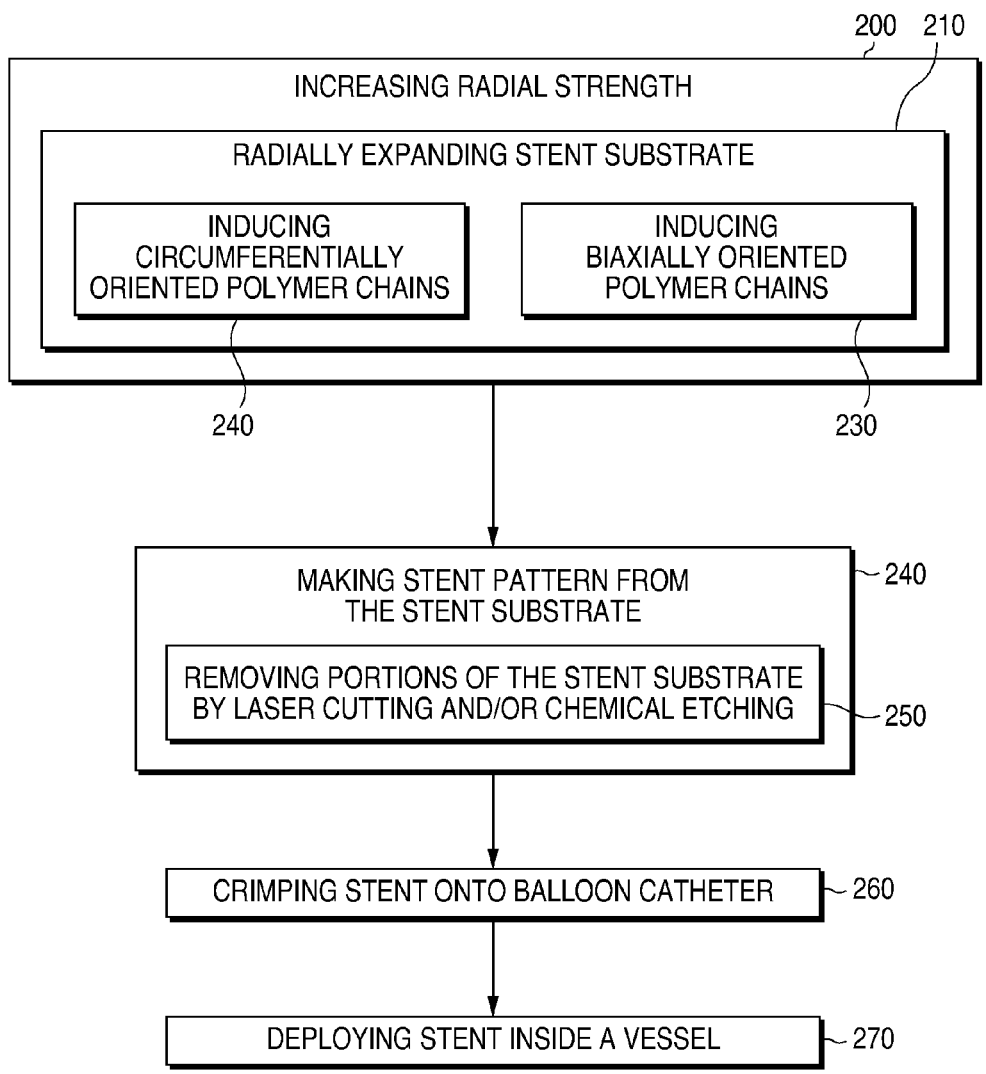
FIG. 2 depicts a process flow diagram in accordance with an embodiment of the present invention.

FIG. 2 shows a method of manufacturing stents in accordance with an embodiment of the present invention. The method comprises increasing 200 the radial strength of the stent substrate in order to eliminate or reduce inward recoil of a stent manufactured from the substrate. The stent substrate can be a polymeric tube or sheet. Increasing 200 the radial strength may include radially expanding 210 the stent substrate. Radial expansion 210 may induce 220 polymer chains in individual stent struts later formed from the substrate to have a preferential orientation in a circumferential direction as compared to an axial direction. The axial direction or orientation corresponds to the overall lengthwise direction of the stent as represented by axis 160 in FIG. 1 and line A-A in FIGS. 3 and 4. The circumferential direction or orientation corresponds to the direction along the circumference of the stent substrate as represented by line B-B in FIGS. 3 and 4 and circle 728 in FIG. 5.

Radial expansion 210 may be achieved by blow molding a stent substrate that is in the form of a polymer tube. Prior to radial expansion 210, the tube has an original inner diameter of $ID_O$. After radial expansion 210, the tube has an outer diameter of $OD_E$. In some embodiments, radial expansion 210 is performed so that the percent radial expansion % RE (equal to $(OD_E/ID_O - 1) \times 100\%$) is between about 300% and 400%, which corresponds to $OD_E$ between about four times $ID_O$ and about five times $ID_O$. In other embodiments, % RE is between about 400% and 500%, which corresponds to $OD_E$ between about five times $ID_O$ and about six times $ID_O$. In yet other embodiments, radial expansion 210 is performed until % RE is about 500%, or greater, which corresponds to $OD_E$ that about six times $ID_O$, or greater.

Polymer chains in a stent substrate may initially have a preferential orientation in the axial direction as a result of extrusion, injection molding, tensile loading, machining, or other process used to form the stent substrate. In some embodiments, radial expansion 210 of a stent substrate having polymer chains with an initial axial orientation will reorient or induce 220 the polymer chains to have a circumferential orientation. In other embodiments, radial expansion 210 of a stent substrate having polymers with an initial axial orientation may induce 230 polymer molecule chains to have a biaxial orientation. In a biaxial orientation, the polymer chains are oriented in a direction that is neither preferentially circumferential nor preferentially axial. In this way, the polymer chains can be oriented in a direction parallel or substantially parallel to the lengthwise axis of individual stent struts so as to increase the overall radial strength of the stent.

Figure 3:
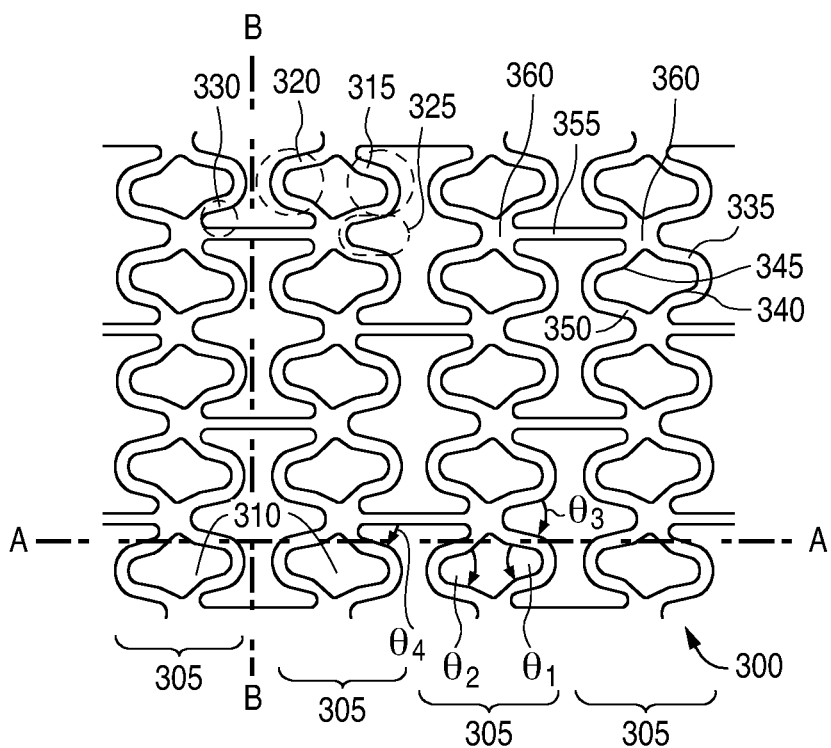
FIG. 3 depicts a stent pattern viewed in a flat or planar state.
Figure 4:
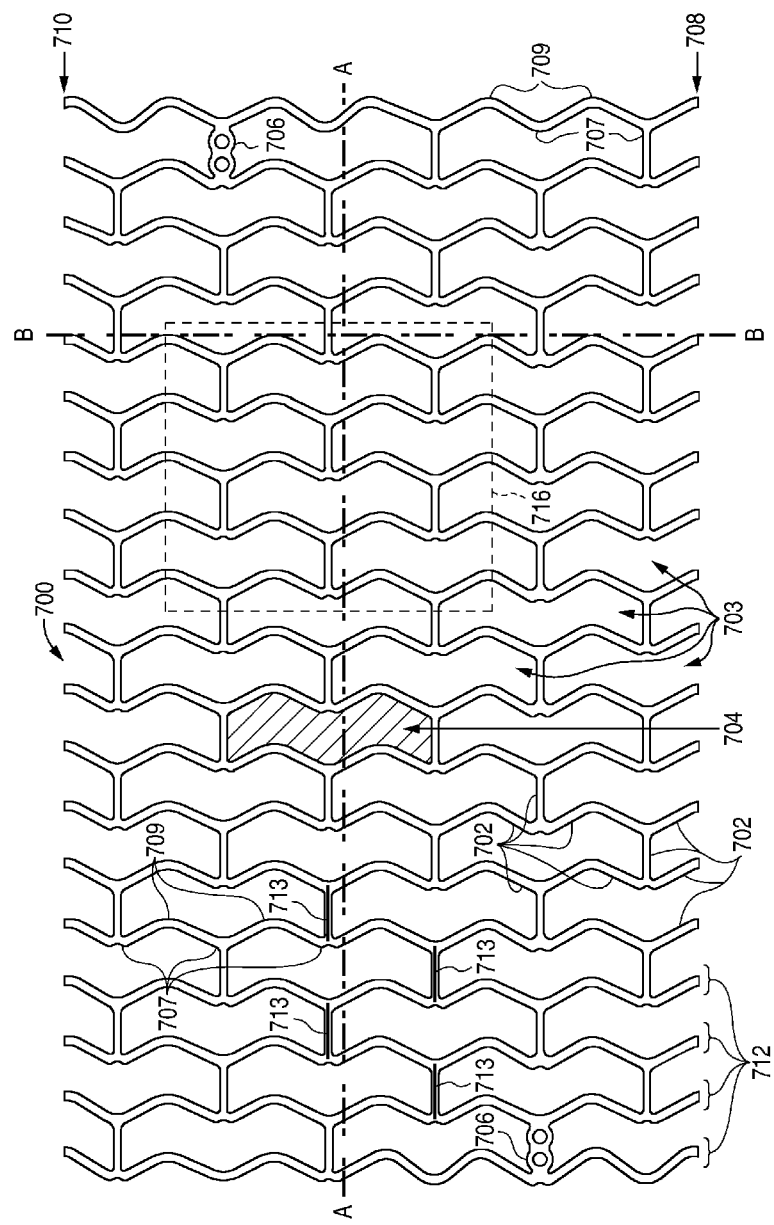
FIG. 4 depicts another stent pattern viewed in a flat or planar state.

The method also includes making 240 a stent pattern from the substrate after inducing polymer chains to have a particular preferential orientation. Making 240 the stent pattern may include removing 250 portions of the substrate by laser cutting and/or chemical etching, leaving only stent struts, bending elements, and other necessary structures. The desired strength, toughness, and/or flexibility of individual structural elements in the stent pattern can achieved by forming such elements parallel or substantially parallel with the orientation of the polymer molecule chains. The stent pattern can be as shown in FIGS. 3 and 4 or variations of FIGS. 3 and 4.

Optionally, after making 240 the stent pattern, the stent may be crimped 260 onto a balloon catheter or other stent delivery device. Prior to or during crimping 260, the stent may be heated to a crimping temperature Tc. In some embodiments, Tc is greater than ambient room temperature Ta to minimize or prevent outward recoil of the stent to a larger diameter after crimping. Outward recoil undesirably increases the delivery profile of the stent and may cause the stent to prematurely detach from the catheter during delivery to a target treatment site within a vessel. Also, Tc is preferably below Tg to reduce or eliminate stress relaxation during crimping. Stress relaxation during or after crimping leads to a greater probability of cracking during subsequent deployment of the stent. To reduce or prevent such cracking, the difference between Tc and Tg can be maximized by increasing Tg through stress induced crystallization.

After manufacturing, the stent can be deployed 270 inside a blood vessel from a crimped diameter to a deployed outer diameter $OD_D$. In some embodiments, $OD_D$ is greater than $OD_E$, the outer diameter as a result of radial expansion of the stent substrate. Preferably, $OD_D$ is selected so that no cracks are formed in the stent during deployment. In some embodiments, $OD_D$ is 3.5 mm (0.1378 in). In other embodiments, $OD_D$ is 4.0 mm (0.1575 in).

If the stent was crimped 260 onto a balloon catheter, the deployment 270 of the stent can include inflating the balloon catheter to urge the stent to move from its crimped configuration to an expanded, deployed configuration. In other embodiments, the stent may be self-expanding and deployment 270 of the stent can include removing a sheath or other constraining device from around the stent to allow the stent to self-expand.

It will be appreciated that the method of FIG. 2 is applicable to many types of bodily lumens or organs. Examples of such organs include, but are not limited to, vascular organs such as, for example, coronary arteries or hepatic veins; renal organs such as, for example, urethras and ureters; biliary organs such as, for example, biliary ducts; pulmonary organs such as, for example, tracheas, bronchi and bronchioles; and gastrointestinal organs such as, for example, esophagi and colons.

FIG. 3 depicts an exemplary stent pattern 300 cut from a polymeric substrate. Stent pattern 300 is shown in a flattened condition so that the pattern can be clearly viewed. When the stent pattern 300 is in a cylindrical form, it forms a radially expandable stent. Stent pattern 300 includes a plurality of cylindrical rings 305 with each ring including a plurality of diamond shaped cells 310. Embodiments of stent pattern 300 may have any number of rings 305 depending on a desired length of a stent. For reference, line A-A extends in an longitudinal or axial direction, which is the same direction of axis 160 in FIG. 1. Diamond shaped cells 310 include bending elements 315 and 320. Stent pattern 300 can also includes bending elements 325 and 330. The angles of bending elements 315, 320, 325, and 330 correspond to angles $\theta_1$, $\theta_2$, $\theta_3$, and $\theta_4$. Angles $\theta_1$, $\theta_2$, $\theta_3$, and $\theta_4$ are equivalent to or about 42, 42, 41, and 21 degrees, respectively. In other embodiments, angles $\theta_1$, $\theta_2$, $\theta_3$ are about 24 degrees to about 29 degrees, and angle $\theta_4$ is about 12 degrees to about 15 degrees. Diamond shaped cells 310 are made up of bar arms 335 and 340 that form bending element 315 and bar arms 345 and 350 that form bending element 320.

When stent 300 is crimped, bending elements 315, 320, 325, and 330 flex inward and angles $\theta_1$, $\theta_2$, $\theta_3$, and $\theta_4$ decrease, allowing the stent to be radially compressed. With respect to bending elements 315, 320, and 325, struts on either side of the bending elements bend toward each other. However, in bending element 330, the strut of the diamond-shaped element tends to bend toward a linking arm 355 which tends to remain relatively parallel to the longitudinal axis during crimping.

Pattern 300 includes linking arms 355 that connect adjacent cylindrical rings. Linking arms 355 are parallel to line A-A and connect adjacent rings between intersection 360 of circumferentially adjacent diamond-shaped elements 310 of one ring and intersection 360 of circumferentially adjacent diamond shaped elements 310 of an adjacent ring. As shown, linking elements connect every other intersection along the circumference.

The curved portions of bending elements experience substantial stress and strain when a stent is crimped and deployed. Therefore high strength and toughness are very important in these regions. Ideally, the most effective polymer chain orientation to improve fracture toughness is along the length of the axis of the strut. Radial expansion imparts orientation and fracture toughness along the circumferential direction, as shown by line B-B.

FIG. 4 shows another stent pattern 700 in accordance with an embodiment of the present invention. The stent pattern 700 includes various struts 702 oriented in different directions and gaps 703 between the struts. Each gap 703 and the struts 702 immediately surrounding the gap 703 defines a closed cell 704. At the proximal and distal ends of the stent, a strut 706 includes depressions, blind holes, or through holes adapted to hold a radiopaque marker that allows the position of the stent inside of a patient to be determined.

One of the cells 704 is shown with cross-hatch lines to illustrate the shape and size of the cells. In the illustrated embodiment, all the cells 704 have the same size and shape. In other embodiments, the cells 704 may vary in shape and size.

The stent pattern 700 is shown in a planar or flattened view for ease of illustration and clarity, although the stent pattern 700 on a stent actually extends around the stent so that line A-A is parallel or substantially parallel to the central axis of the stent. The pattern 700 is illustrated with a bottom edge 708 and a top edge 710. On a stent, the bottom edge 708 meets the top edge 710 so that line B-B forms a circle around the stent. In this way, the stent pattern 700 forms sinusoidal hoops or rings 712 that include a group of struts arranged circumferentially. The rings 712 include a series of crests 707 and troughs 709 that alternate with each other. The sinusoidal variation of the rings 712 occurs primarily in the axial direction, not in the radial direction. That is, all points on the outer surface of each ring 712 are at the same or substantially the same radial distance away from the central axis of the stent.

Still referring to FIG. 4, the rings 712 are connected to each other by another group of struts that have individual lengthwise axes 713 parallel or substantially parallel to line A-A. The rings 712 are capable of being collapsed to a smaller diameter during crimping and expanded to their original diameter or to a larger diameter during deployment in a vessel.

In other embodiments, the stent may have a different number of rings 712 and cells 704 than what is shown in FIG. 4. The number of rings 712 and cells 704 may vary depending on the desired axial length and deployed diameter of the stent. For example, a diseased segment of a vessel may be relatively small so a stent having a fewer number of rings can be used to treat the diseased segment.

Figure 5:
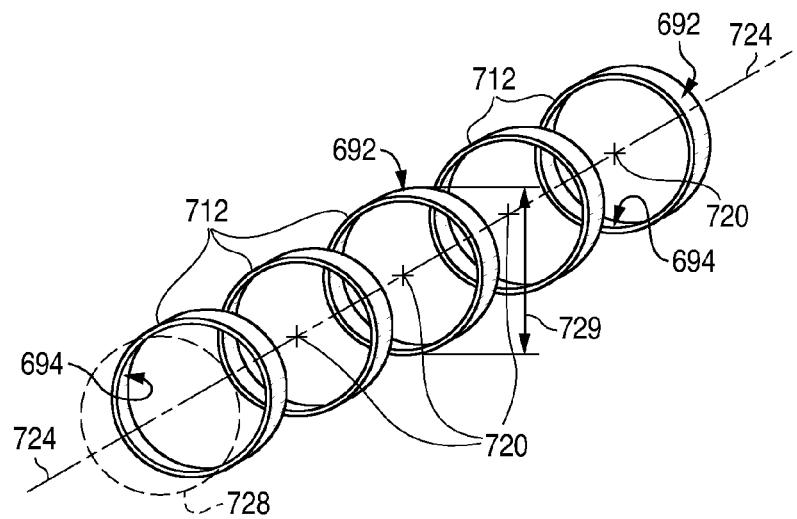
FIG. 5 depicts a simplified view of the stent pattern of FIG. 4 in a cylindrical state.
Figure 6:
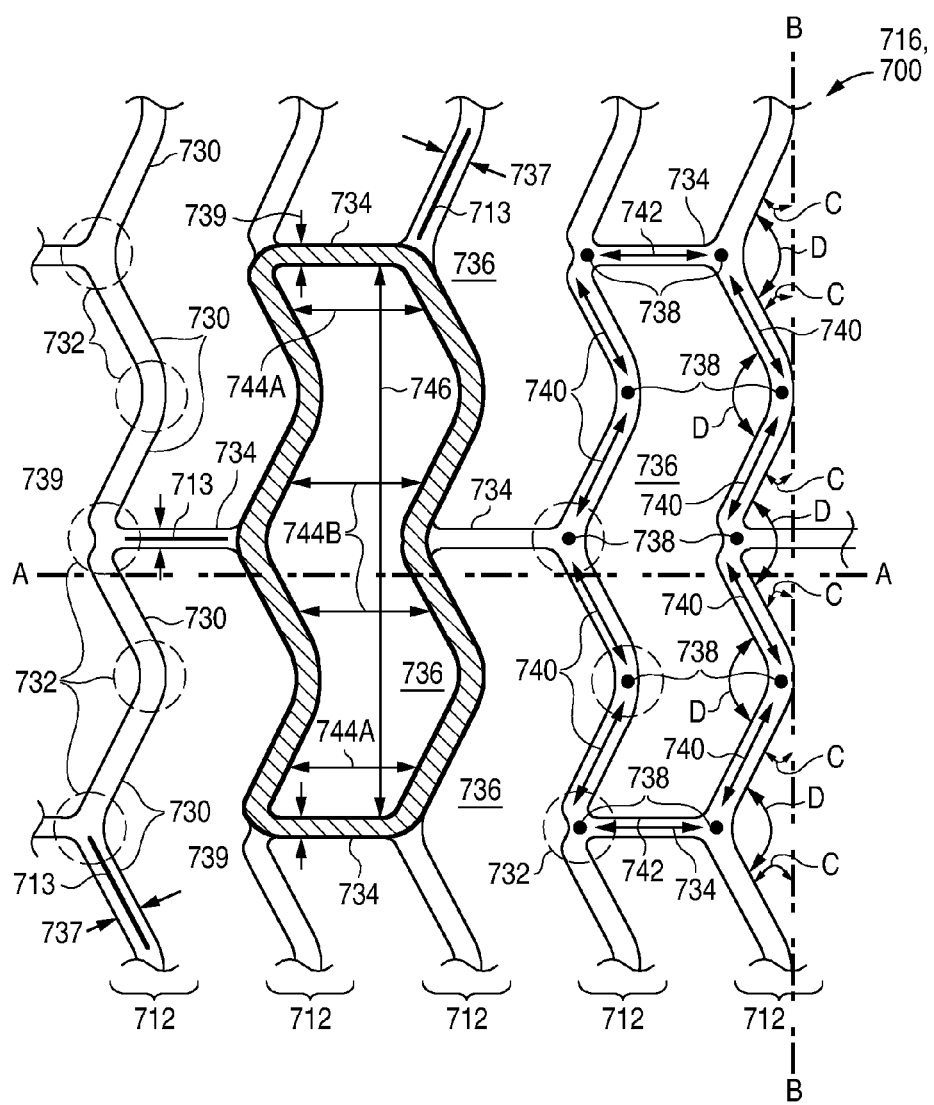
FIG. 6 depicts a detailed view of a portion of the stent pattern of FIG. 4, showing rings in a non-deformed configuration, the rings having an initial diameter.

FIG. 5 shows a simplified diagram of the stent pattern 700 in the form of a cylindrical tube. The sinusoidal variation of the rings 712 and the struts linking the rings to each other are omitted for clarity. The rings 712 have center points 720. At least two of the center points 720 define the central axis 724 of the stent. The central axis 724 and line A-A in FIGS. 4 and 6 are parallel or substantially parallel to each other. The rings have an abluminal surface 692 and a luminal surface 694. The abluminal surface 692 faces outward and normally contacts the wall of the anatomical lumen in which the stent is deployed. The luminal surface 694 faces inward toward the center of the lumen when deployed.

FIG. 6 shows a detailed view of a portion 716 of the stent pattern 700 of FIG. 4. The rings 712 include linear ring struts 730 and curved hinge elements 732. The ring struts 730 are connected to each other by the hinge elements 732. In some embodiments, the ring struts and hinge elements are formed from a polymeric substrate that was radially expanded in the circumferential direction represented by a dotted circle 728 in FIG. 5 and line B-B in FIGS. 4 and 6.

Radial expansion of the substrate used to form the stent pattern 700 is preferably between about 300% and about 700%, which corresponds to $OD_E$ that is between about four to about eight times $ID_O$. In some embodiments, radial expansion is between about 400% and about 600%, which corresponds to $OD_E$ that is between about five to about seven times $ID_O$. In other embodiments, radial expansion is at or about 500%, which corresponds to $OD_E$ that is at or about six times $ID_O$.

The hinge elements 732 are adapted to flex, which allows the rings 712 to move from a non-deformed configuration to a deformed configuration. As used herein, "non-deformed configuration" refers to the state of the rings prior to being crimped to a smaller diameter for delivery through an anatomical lumen. For example, in embodiments in which a stent is formed by laser cutting a radially expanded polymer tube, the non-deformed configuration is the state of the rings after radial expansion of the polymer tube and laser cutting of the polymer tube to form the rings. As used herein, "deformed configuration" refers to the state of the rings upon some type of deformation, such as crimping or deployment.

FIGS. 3-6 show the rings 712 in the non-deformed configuration. Referring to FIG. 5, the rings 712 have an initial outer diameter 729 when in the non-deformed configuration. In some embodiments, the initial outer diameter 729 of the rings 712 is equivalent to or substantially equivalent to $OD_E$, the outer diameter of the stent substrate after the stent substrate is radially expanded.

Referring again to FIG. 6, line B-B lies on a reference plane perpendicular to the central axis 724 (FIG. 5). When the rings 712 are in the non-deformed configuration, as shown in FIG. 6, each ring strut 730 is oriented at a non-zero angle C relative to the reference plane. The non-zero angle C is less than 40 degrees in the illustrated embodiment. Preferably, the non-zero angle C is less than 35 degrees, and more narrowly the angle C is between about 25 degrees and about 28 degrees. In other embodiments, the angle C can have other values.

Also, the ring struts 730 are oriented at an interior angle D relative to each other. The interior angle D is greater than 100 degrees in the illustrated embodiment. Preferably, the interior angle D is greater than 110 degrees, and more narrowly, the angle D is between about 124 degrees and about 130 degrees. In other embodiments, the interior angle D can have other values.

Referring once again to FIG. 6, the stent also includes link struts 734 connecting the rings 712 together. The link struts 734 are oriented parallel or substantially parallel to line A-A and the central axis 724 (FIG. 5). The ring struts 730, hinge elements 732, and link struts 734 define a plurality of W-shaped closed cells 736. The boundary or perimeter of one W-shaped cell 736 is darkened in FIG. 6 for clarity. The W-shapes appear rotated 90 degrees counterclockwise. Each of the W-shaped cells 736 is immediately surrounded by six other W-shaped cells 736, meaning that the perimeter of each W-shaped cell 736 merges with a portion of the perimeter of six other W-shaped cells 736. Stated another way, each W-shaped cell 736 abuts or touches six other W-shaped cells 736.

The perimeter of each W-shaped cell 736 includes eight of the ring struts 730, two of the link struts 734, and ten of the hinge elements 732. Four of the eight ring struts form a proximal side of the cell perimeter and the other four ring struts form a distal side of the cell perimeter. The opposing ring struts on the proximal and distal sides are parallel or substantially parallel to each other.

Figure 10:
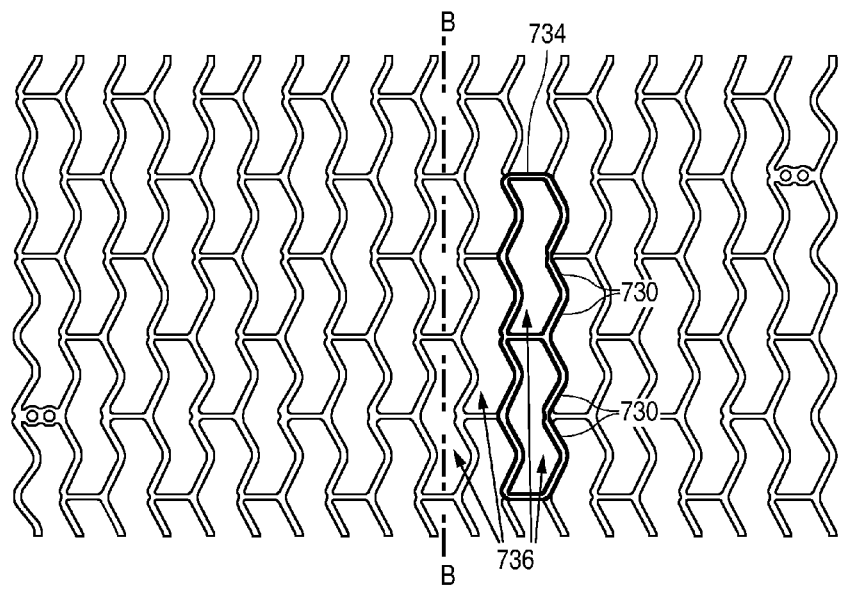
FIG. 10 depicts a stent pattern viewed in a flat or planar state, the stent pattern having W-shaped cells having varying sizes in the circumferential direction.

Within each of the hinge elements 732 there is an intersection point 738 toward which the ring struts 730 and link struts 734 converge. There is an intersection point 738 adjacent each end of the ring struts 730 and link struts 734. Distances 740 between the intersection points adjacent the ends of rings struts 730 are the same or substantially the same for each ring strut 730. In other embodiments, such as shown in FIG. 10, some of the ring struts 730 may be longer than other ring struts 730 so that distances 740 may vary. For example, distances 740 may vary to allow for a variation in mechanical characteristics at different portions of the stent.

Figure 11:
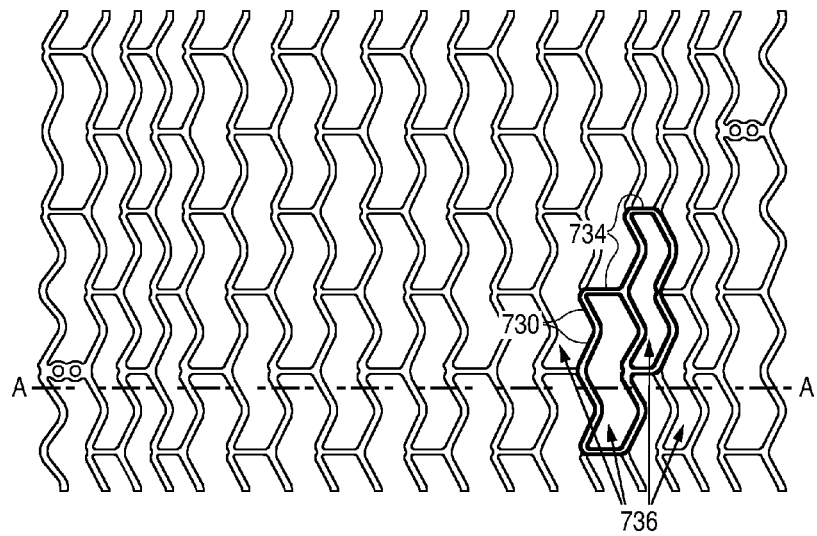
FIG. 11 depicts a stent pattern viewed in a flat or planar state, the stent pattern having W-shaped cells having varying sizes in the axial direction.

Referring again to FIG. 6, distances 742 between the intersection points adjacent the ends of horizontal link struts 734 are the same or substantially the same for each link strut 734. In other embodiments, such as shown in FIG. 11, some of the link struts 734 may be longer than other link struts 734 so that distances 742 may vary to allow for a variation in mechanical characteristics at different portions of the stent.

Also, distances 740 are the same or substantially the same as distances 742. In other embodiments, distances 740 and 742 are different from each other to allow for a variation in mechanical characteristics at different portions of the stent.

The ring struts 730 have widths 737 that are uniform along the individual lengthwise axis 713 of the ring strut. The link struts 734 have widths 739 that are also uniform along the individual lengthwise axis 713 of the link strut.

As shown in FIG. 6, the interior space of each W-shaped cell 736 has an axial dimension 744 parallel to line A-A and a circumferential dimension 746 parallel to line B-B. The axial dimension 744 is constant or substantially constant with respect to circumferential position. That is, axial dimensions 744A adjacent the top and bottom ends of the cells 736 are the same or substantially the same as axial dimensions 744B further away from the ends. The constant axial dimension 744 provides an improved strut distribution compared to the stent pattern of FIG. 3.

In the illustrated embodiment of FIG. 6, axial and circumferential dimensions 744 and 746 are the same among the W-shaped cells 736. In other embodiments, the axial dimension 744 and/or circumferential dimension 746 may differ among cells 736 to allow for a variation in mechanical characteristics at different portions of the stent.

FIGS. 7 and 8 show a portion of one ring 712 in two different deformed configurations. In FIG. 7, the ring 712 has been radially compressed to a diameter less than its initial outer diameter 729 (FIG. 5), such as when the stent is crimped onto a catheter. During such compression, the ring struts 730 pivot about the hinge elements 732 so that the ring struts 730 fold toward each other and become oriented at an angle E relative to the reference plane represented by line B-B. Angle E is greater than corresponding angle C in FIG. 6 which shows rings 712 in the non-deformed configuration. Also, the ring struts 730 are oriented at an interior angle F relative to each other. Angle F is less than corresponding angle D in FIG. 6.

In FIG. 8, the ring 712 has been radially expanded, after manufacturing, to a deployed configuration. Radial expansion of the rings 712 is not to be confused with radial expansion of the stent substrate during manufacturing. When the ring 712 is radially expanded, ring struts 730 pivot about the hinge elements 732 and the ring struts 730 become oriented at an angle G relative to the reference plane represented by line B-B. When the ring 712 is expanded to a diameter greater than its non-deformed initial diameter 729 (FIG. 5), angle G is less than corresponding angle C in FIG. 6. Also, the ring struts 730 are oriented at an interior angle H relative to each other. Angle H is greater than corresponding angle D in FIG. 6.

Figure 9:
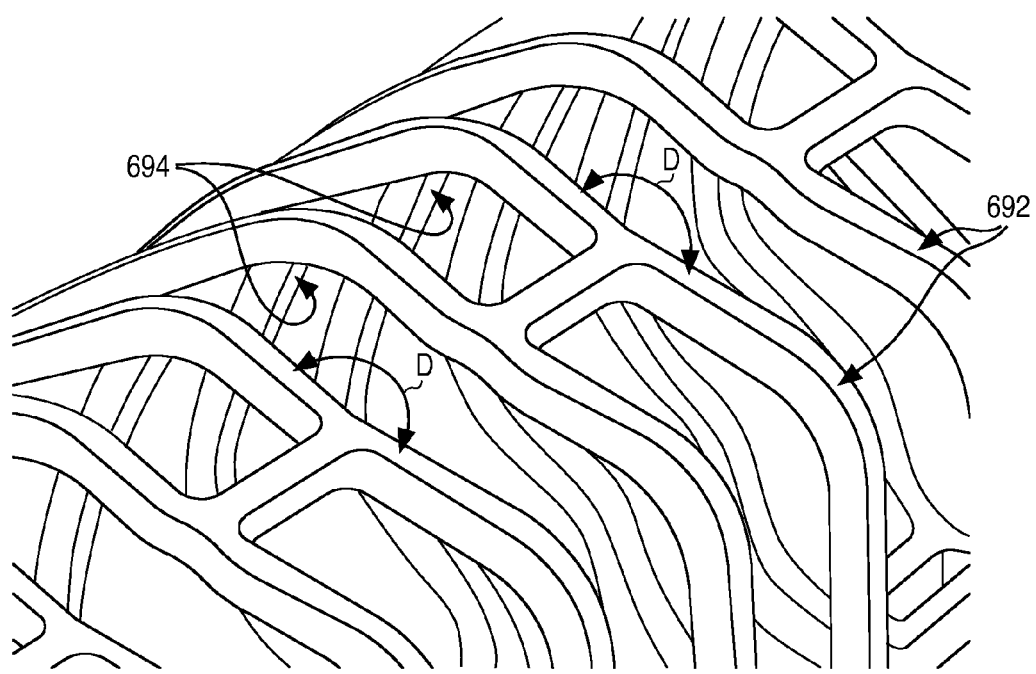
FIG. 9 depicts a photographic image of a stent having the stent pattern of FIG. 4.

A test was performed to study long term lumen patency using different stent patterns formed from polymer tube substrates that were radially expanded during manufacturing. Case 1 corresponds to a stent having the stent pattern of FIG. 2 cut from a polymer tube substrate that was previously radially expanded 300% to a diameter of 2.13 mm (0.084 inches). Case 2 corresponds to a stent having the stent pattern of FIGS. 4 and 6 cut from a polymer tube substrate that was previously radially expanded 500% to a diameter of 3.48 mm (0.137 inches). In both cases, the polymer tube was an extruded tube of poly(L-lactide), a bioabsorbable polymer. FIG. 9 is a photograph of a portion of the stent of Case 2.

In Case 1, ring struts 335, 340, 345, and 350, when in the non-deformed configuration, were at about 75 degrees to about 78 degrees relative to the circumferential direction, that is the direction of radial expansion. Also, ring struts 335 and 345 were oriented relative to ring struts 340 and 350 at interior angles ($\theta_1$ and $\theta_3$ in FIG. 3) of about 24 degrees to about 29 degrees.

In Case 2, ring struts 730, when in the non-deformed configuration, were at 25 degrees to 28 degrees from the circumferential direction. Also, ring struts 730 were oriented relative to each other at an interior angle (angle D in FIG. 6) of about 124 degrees to about 130 degrees.

Compared to Case 1, Case 2 exhibited less inward recoil (decrease in diameter) after deployment, resulting in larger lumens and better stent apposition or contact with surrounding tissue. The results of the test indicate that 500% radial expansion combined with struts arranged in the pattern of FIGS. 4 and 6 (Case 2) provided greater radial strength than 300% radial expansion combined with struts arranged in the pattern of FIG. 3 (Case 1). The results were unexpected in that excessive radial expansion of the substrate is known to cause an increase in strut fractures during crimping or upon deployment, and that excessively large interior angles are known to prevent stents from crimping easily and in a controlled manner.

It is believed that the polymer chains in Case 1 do not readily line up with the rings as compared to Case 2, leading to a stent that is less resistant to mechanical creep deformation as compared to Case 2. With 500% radial expansion in Case 2, the polymer chains are substantially circumferentially oriented. The interior angles between stent struts in Case 2 allow the stent struts to line up well with the circumferentially oriented polymer chains. It is also believed that smaller interior angles than those in Case 2 would increase the likelihood of fractures since expansion loads would be applied against the "grain" of the substrate, that is, against the circumferential orientation of the polymer chains.

In other tests, stents were made from tubes of poly(L-lactide) substrate that were radially expanded to different levels, namely 400%, 500%, 600%, and 700%. The stents were crimped at different crimping temperatures, deployed, then inspected for fractures. At a crimping temperature of about 50° C., the group of stents made from 500% radially expanded tubes had the lowest average number of fractures. At crimping temperatures of about 30° C., 50° C., and 60° C., the group of stents made from 700% radially expanded tubes had the highest average number of fractures.

It will be appreciated that the above disclosed stent patterns may be applied to non-polymer stent substrates as well. A non-polymer substrate of a stent may be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

While several particular forms of the invention have been illustrated and described, it will also be apparent that various modifications can be made without departing from the scope of the invention. For example, the W-shaped cells 736 may vary in size in the circumferential direction (line B-B), such as shown in FIG. 10. As a further example, the W-shaped cells 736 may vary in size in the axial direction (line A-A), such as shown in FIG. 11. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. An endoprosthesis comprising:
    linear ring struts, link struts, and curved hinge elements, the ring struts connected to each other by the hinge elements, the ring struts and the hinge elements defining a plurality of rings, the rings connected to each other by the link struts, the hinge elements adapted to allow the rings to move from a non-deformed configuration to a deformed configuration, the non-deformed configuration corresponding to the state of the rings before crimping, the deformed configuration corresponding to the state of the rings after crimping,
    wherein the ring struts, hinge elements, and link struts define a plurality of W-shaped closed cells, each W-shaped cell touching six other W-shaped cells, each W-shaped cell having a perimeter that includes eight of the ring struts, two of the link struts, and ten of the hinge elements, and wherein when the rings are in the non-deformed configuration, the ring struts are oriented relative to each other at an interior angle greater than 100 degrees.

2. The endoprosthesis of claim 1, wherein when the rings are in the non-deformed configuration, the interior angle is between about 124 degrees and about 130 degrees.

3. The endoprosthesis of claim 1, wherein the ring struts and hinge elements are formed from a radially expanded polymer tube having an outer diameter greater than or equivalent to about five times an inner diameter of the tube prior to expansion.

4. The endoprosthesis of claim 1, wherein the ring struts and hinge elements are formed from a radially expanded polymer tube having an outer diameter greater than or equivalent to about six times an inner diameter of the tube prior to expansion.

5. The endoprosthesis of claim 4, wherein when the rings are in the non-deformed configuration, each ring strut is oriented at an angle less than about 40 degrees relative to the direction in which the polymer tube was radially expanded.

6. The endoprosthesis of claim 1, wherein each ring has a center point, at least two of the center points defining a central axis, and the link struts are oriented parallel or substantially parallel to the central axis when the rings are in the non-deformed configuration.

7. An endoprosthesis comprising:
    ring struts and link struts formed from a radially expanded polymer tube having an outer diameter after expansion that is greater than about four times an inner diameter of the polymer tube prior to expansion, the ring struts defining a plurality of rings capable of moving from a non-deformed configuration to a deformed configuration, each ring having a center point, at least two of the center points defining a central axis, the link struts oriented parallel or substantially parallel to the central axis and connecting the rings together, the link struts and the ring struts defining W-shaped closed cells, each W-shaped cell abutting six other W-shaped cells, each W-shaped cell having a perimeter that includes eight of the ring struts and two of the link struts,
    wherein when the rings are in the non-deformed configuration, the ring struts are oriented relative to each other at an interior angle greater than 100 degrees.

8. The endoprosthesis of claim 7, wherein the interior angle is between about 124 degrees and about 130 degrees when the rings are in the non-deformed configuration.

9. The endoprosthesis of claim 7, wherein the outer diameter of the polymer tube after expansion is greater than or equivalent to about six times the inner diameter of the polymer tube prior to expansion.

10. The endoprosthesis of claim 9, wherein when the rings are in the non-deformed configuration, each ring strut is oriented at angle between about 25 degrees and about 28 degrees relative to a plane perpendicular to the central axis.

11. The endoprosthesis of claim 7, wherein the link struts and the ring struts are equivalent or substantially equivalent in length.

12. The endoprosthesis of claim 7, wherein the ring struts on each ring define a series of crests and troughs that alternate with each other, each crest on each ring connected by one of the link struts to another crest on another ring.

13. The endoprosthesis of claim 7, wherein the polymer tube has an outer surface and an inner surface, the rings have an abluminal surface and a luminal surface, the abluminal surface corresponding to the outer surface of the polymer tube, the luminal surface corresponding to the inner surface of the polymer tube.

14. The endoprosthesis of claim 7, wherein the non-deformed configuration corresponds to the state of the rings before crimping, the deformed configuration corresponds to the state of the rings after crimping.

* * * * *